United States Patent [19]

Sommer et al.

[11] 4,241,211
[45] Dec. 23, 1980

[54] CHEMICAL AGENTS

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 682,722

[22] Filed: Nov. 1, 1967

[51] Int. Cl.³ .................................. C07D 213/62
[52] U.S. Cl. ............................ 546/261; 424/263
[58] Field of Search .................. 260/296, 482 C; 424/263; 546/291

[56] References Cited

U.S. PATENT DOCUMENTS 3,188,955   6/1965   Brown .................................. 102/24

*Primary Examiner*—Leland A. Sebastian
*Attorney, Agent, or Firm*—Nathan Edelberg; Robert P. Gibson; Harold H. Card, Jr.

[57] ABSTRACT

New chemical compounds, bis-quaternary carbamates, having the generic formula:

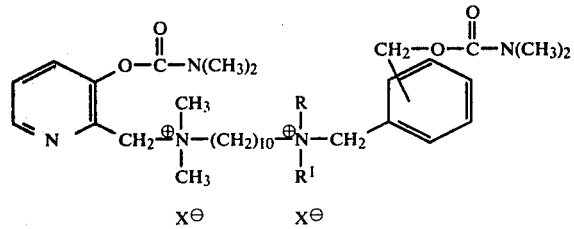

wherein X is one equivalent of an anion selected from monovalent or polyvalent anions; wherein R and R' are aliphatic radicals selected from the group consisting of methyl, ethyl, propyl, isopropyl, and butyl; and wherein the dimethylcarbamoxymethyl group is in the ortho, meta or para position of the phenyl ring, and having utility as toxic agents.

2 Claims, No Drawings

CHEMICAL AGENTS

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quaternary compounds, the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields wherein said products are well suited for industrial scale manufacture.

Other objects of and u

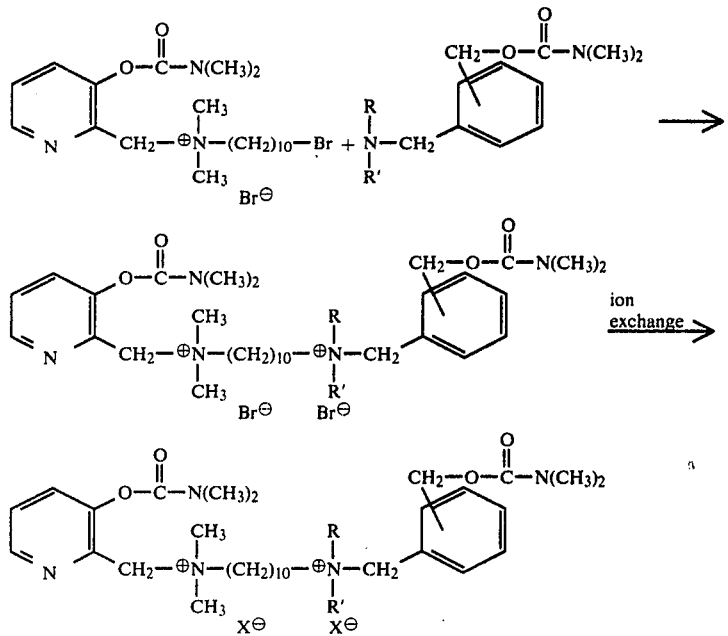

wherein X is a halide ion, preferably bromide, and wherein R and R' are as defined above.

If compounds are desired in which X is other than a halide ion, the above quaternary compounds are treated with the desired acid by simple exchange reactions as set forth below.

EXAMPLE

N-(10-bromodecyl)-N-(3-dimethylcarbamoxy-α-picolinyl)-N,N-dimethylammonium bromide (1.0 g) and N-(4-dimethylcarbamoxymethyl) benzyl-N,N-dimethylamine (0.75 g) were dissolved in 5 ml of acetonitrile and the solution allowed to stand at room temperature for about 21 days. Acetone (about 50 ml) was then added causing an oily material to precipitate. The solvent was decanted, and the remaining oil was dissolved in the minimum amount of acetonitrile. The viscous oily material was reprecipitated by the addition of about 50 ml of acetone. The acetone was again decanted and the gummy residue dissolved in acetonitrile (50 ml). This solution was treated with decolorizing carbon and then concentrated to a few milliliters. The concentrate was placed for about 24 hours in an apparatus that was kept under reduced pressure (about 0.5 mm) at room temperature. The product, 1-[N-(4-dimethylcarbamoxymethyl)benzyl-N,N-dimethylammonio]-10-[N-(3-dimethylcarbamoxy-α-picolinyl)-N,N-dimethylammonio]-decane dibromide (1.2 g) was obtained as a deliquescent white crystalline material. Because of its deliquescency a sample of the compound was converted to and analyzed as the tetraphenylboronate salt. The above dibromide salt was dissolved in water, and to this solution an aqueous solution of sodium tetraphenylboron (in molar excess) was added. The solid that formed was collected on a filter, washed a few times with water, and then dried. The tetraphenylboronate salt melted between 67°–70° C.

Analysis for $C_{82}H_{97}B_2N_5O_4$; Calcd: C, 79.5; H, 7.9; N, 5.7. Found: C, 79.6; H, 8.2; N, 5.5.

| | Toxicity IV $LD_{50}$ | |
|---|---|---|
| Rabbits | | Mice |
| 0.008 mg/kg | | 0.018 mg/kg |

Method of Preparation of N-(10-bromodecyl)-N-(3-dimethylcarbamoxy-α-picolinyl)-N,N-dimethylammonium bromide A solution of 62.3 g of 2-dimethylaminomethyl-3-dimethylcarbamoxypyridine and 251 g of 1,10 dibromodecane was refluxed for about 7 days in 1 liter of anhydrous ether. The product that formed was collected on a filter, washed with two 100 ml portions of anhydrous ether, and dissolved in 1 liter of acetone. The acetone solution was treated with decolorizing carbon and filtered. The filtrate was concentrated under reduced pressure to approximately 200 ml. Ether was added until the solution became turbid. The mixture was then seeded and chilled overnight. The resultant crystalline product was collected and further purified by recrystallization from ethyl acetate. The pure product was dried in vacuo for about 2 hours, yielding 76 g of material, m.p. 90°–92° C.

Analysis for $C_{21}H_{37}Br_2N_3O_2$; Calcd: C, 48.2; H, 7.1; Br⁻(ionic), 15.3; O, 6.1. Found: C, 48.2; H, 7.0; $Br^{31}$ (ionic), 15.2; O, 6.2.

The compounds that are representative of our invention are listed below by name and chemical structure.

1-[N-(2-dimethylcarbamoxymethyl)benzyl-N,N-dimethylammonio]-10-[N-(3-dimethylcarbamoxy-α-picolinyl)-N,N-dimethylammonio]decane dibromide.

1-[N-(4-dimethylcarbamoxymethyl)benzyl-N,N-dimethylammonio]-10-[N-(3-dimethylcarbamoxy-α-picolinyl)-N,N-dimethylammonio]decane dibromide.

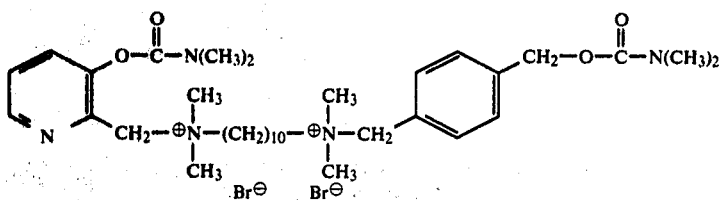

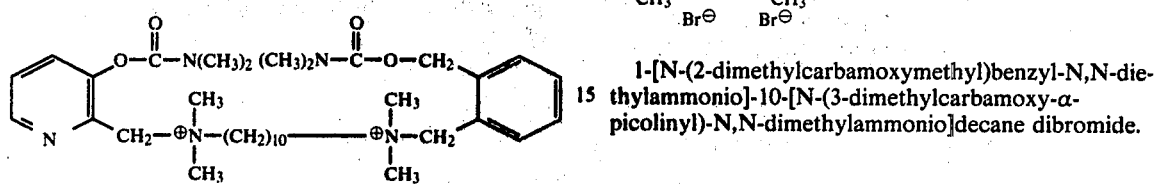

1-[N-(2-dimethylcarbamoxymethyl)benzyl-N,N-diethylammonio]-10-[N-(3-dimethylcarbamoxy-α-picolinyl)-N,N-dimethylammonio]decane dibromide.

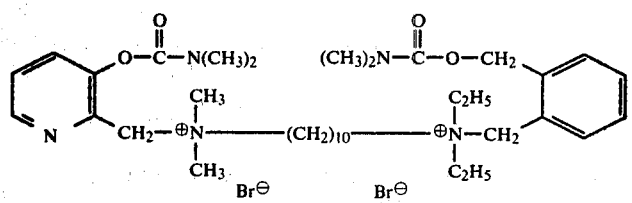

1-[N-(3-dimethylcarbamoxymethyl)benzyl-N-ethyl-N-methylammonio]-10-[N-(3-dimethylcarbamoxy-α-picolinyl)-N,N-dimethylammonio]decane dibromide.

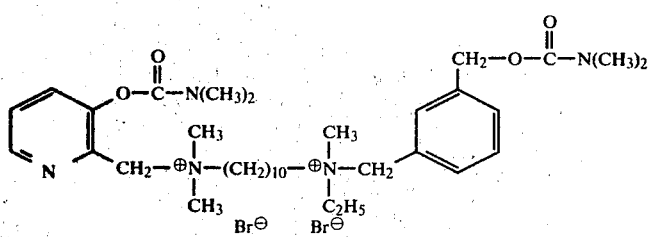

1-[N-(4-dimethylcarbamoxymethyl)benzyl-N-methyl-N-propylammonio]-10-[N-(3-dimethylcarbamoxy-α-picolinyl)-N,N-dimethylammonio]decane dibromide.

1-[N-(3-dimethylcarbamoxymethyl)benzyl-N,N-dimethylammonio]-10-[N-(3-dimethylcarbamoxy-α-picolinyl)-N,N-dimethylammonio]decane dibromide.

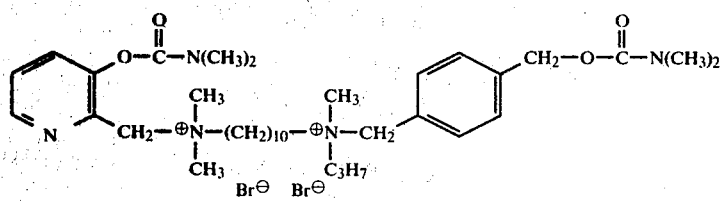

1[N-(2-dimethylcarbamoxymethyl)benzyl-N-butyl-N-methylammonio]-10-[N-(3-dimethylcarbamoxy-α-picolinyl)-N,N-dimethylammonio]decane dibromide.

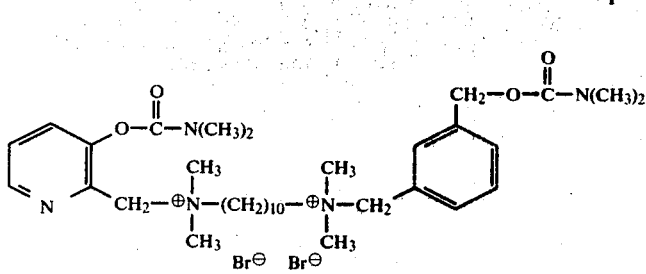

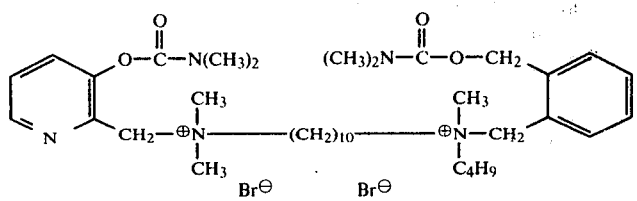

1-[N-(2-dimethylcarbamoxymethyl)benzyl-N-isopropyl-N-methylammonio]-10-[N-(3-dimethylcarbamoxy-α-picolinyl)-N,N-dimethylammonio]decane dibromide.

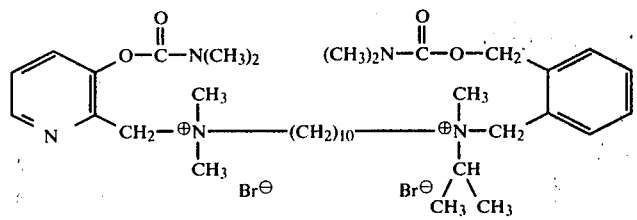

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus the halogen ions can be exchanged with other anions of relatively strong monovalent or polyvalent acid by conventional methods. For example, if $X^-$ is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, nitrate, tetraphenylboronate, and hydrogen sulfate. Representative examples of these additional end products are: 1-[N-(2-dimethylcarbamoxymethyl)benzyl-N,N-dimethylammonio]-10-[N-(3-dimethylcarbamoxy-α-picolinyl)-N,N-dimethylammonio]decane di(hydrogen oxalate).

1-[N-(2-dimethylcarbamoxymethyl)benzyl-N,N-dimethylammonio]-10-[N-(3-dimethylcarbamoxy-α-picolinyl)-N,N-dimethylammonio]decane diperchlorate.

1-[N-(2-dimethylcarbamoxymethyl)benzyl-N,N-dimethylammonio]-10-[N-(3-dimethylcarbamoxy-α-picolinyl)-N,N-dimethylammonio]decane dinitrate.

1-[N-(2-dimethylcarbamoxymethyl)benzyl-N,N-dimethylammonio]-10-[N-(3-dimethylcarbamoxy-α-picolinyl)-N,N-dimethylammonio]decane di(tetraphenylboronate).

1-[N-(2-dimethylcarbamoxymethyl)benzyl-N,N-dimethylammonio]-10-[N-(3-dimethylcarbamoxy-α-picolinyl)-N,N-dimethylammonio]decane di(hydrogen sulfate).

We claim:

1. New chemical compounds having the generic formula:

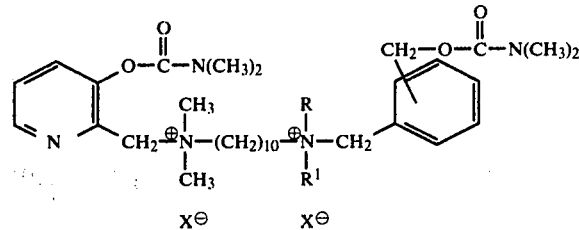

wherein X is one equivalent of an anion selected from monovalent and polyvalent anions, said anions being selected from the group consisting of halide, hydrogen oxalate, perchlorate, hydrogen sulfate, nitrate, and tetraphenylboronate; R and R' are aliphatic radicals selected from the group consisting of methyl, ethyl, propyl, isopropyl, and butyl; and the dimethylcarbamoxymethyl group is in the position selected from ortho, meta, and para of the phenyl ring.

2. New chemical compounds selected from the group of compounds having the names:

1-[N-(2-dimethylcarbamoxymethyl)benzyl-N,N-dimethylammonio]-10-[N-(3-dimethylcarbamoxy-α-picolinyl)-N,N-dimethylammonio]decane dibromide;

1-[N-(3-dimethylcarbamoxymethyl)benzyl-N,N-dimethylammonio]-10-[N-(3-dimethylcarbamoxy-α-picolinyl)-N,N-dimethylammonio]decane dibromide; and 1-[N-(4-dimethylcarbamoxymethyl)benzyl-N,N-dimethylammonio]-10-[N-(3-dimethylcarbamoxy-α-picolinyl)-N,N-dimethylammonio]decane dibromide.

* * * * *